United States Patent [19]
Parker

[11] Patent Number: 5,221,270
[45] Date of Patent: Jun. 22, 1993

[54] SOFT TIP GUIDING CATHETER

[75] Inventor: Fred T. Parker, Bloomington, Ind.

[73] Assignee: Cook Incorporated, Bloomington, Ind.

[21] Appl. No.: 725,754

[22] Filed: Jun. 28, 1991

[51] Int. Cl.⁵ .......................................... A61M 25/00
[52] U.S. Cl. .................................. 604/282; 604/280; 604/264
[58] Field of Search ............... 604/280, 282, 604/264, 103, 95, 96; 128/656–658

[56] References Cited

U.S. PATENT DOCUMENTS

| | | | |
|---|---|---|---|
| 3,529,633 | 9/1970 | Vaillancourt. | |
| 4,385,635 | 5/1983 | Ruiz | 128/658 |
| 4,563,181 | 1/1986 | Wijayarathna et al. | 604/280 |
| 4,636,346 | 1/1987 | Gold et al. | 604/280 |
| 4,863,442 | 9/1989 | DeMello et al. | 604/282 |
| 4,898,591 | 2/1990 | Jang et al. | 604/282 |
| 5,017,259 | 5/1991 | Kohsai | 604/280 |
| 5,078,702 | 1/1992 | Pomeranz | 604/282 |
| 5,085,649 | 2/1992 | Flynn | 604/282 |

FOREIGN PATENT DOCUMENTS

| | | |
|---|---|---|
| 0273618 | 7/1988 | European Pat. Off. . |
| 0303487 | 2/1989 | European Pat. Off. . |

Primary Examiner—C. Fred Rosenbaum
Assistant Examiner—Ronald K. Stright, Jr.
Attorney, Agent, or Firm—Richard J. Godlewski

[57] ABSTRACT

A soft tip guiding catheter for atraumatic insertion into delicate, tortuous coronary vessels and introduction of an angioplasty balloon catheter therethrough. The guiding catheter includes a main tubular portion and a soft tubular tip with respective, matching external and internal tapers for increasing the contact area of the thermal bond. The outer and inner diameters of the main portion are uniform and match the respective outer and inner diameters of the soft tip for providing a uniform outer catheter surface and a continuous, uniform catheter passageway surface. The tapers further provide for a gradual change in durometer between the main portion and soft tip. The main portion preferably includes an inner layer of lubricous material, an outer layer of a polyether block amide, and a reinforcing braid positioned therebetween. The layers of the main portion provide a thin catheter wall with pushability, torquability, and kink resistance. The composite durometer of the main portion is harder than the durometer of the soft tip, which comprises a combination of polyether block amide material and tungsten for increasing the radiopacity thereof.

20 Claims, 1 Drawing Sheet

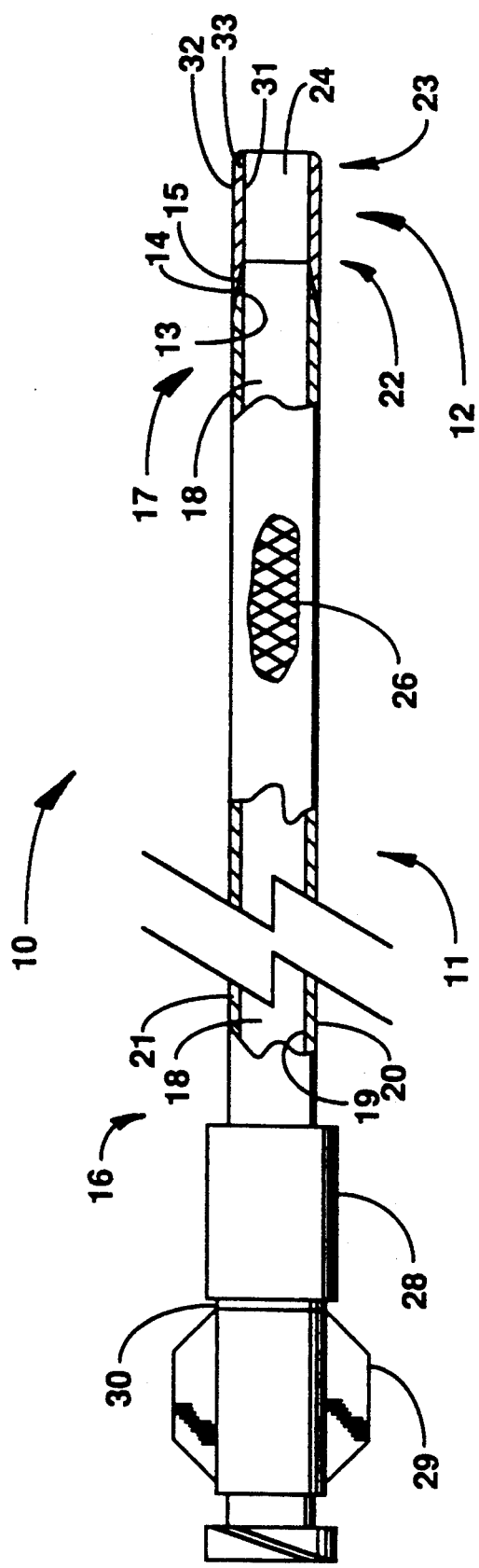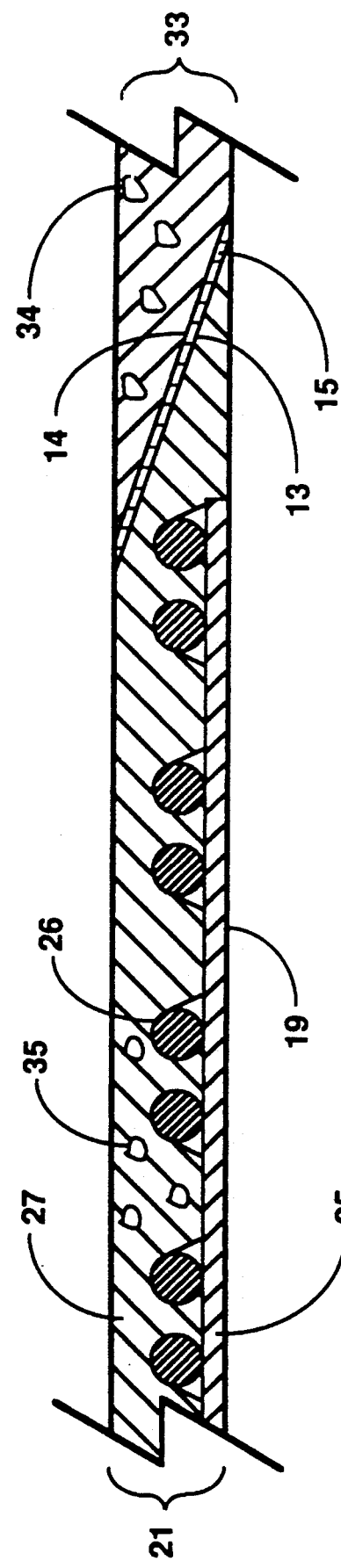

SOFT TIP GUIDING CATHETER

TECHNICAL FIELD

This invention relates generally to guiding catheters and, in particular, to a guiding catheter with a soft distal tip.

BACKGROUND OF THE INVENTION

Guiding catheters are commonly used during coronary angioplasty procedures for delivering a balloon catheter to a treatment site in a coronary vessel. To move a guiding catheter safely through the vascular system and into the delicate coronary vessels, the guiding catheter must have a soft distal tip. The soft distal tip minimizes the risk of causing trauma to a vessel, freeing plaque from a vessel wall, puncturing a vessel, or creating embolisms in the bloodstream.

One nonanalogous, nonbraided angiographic catheter comprises an inner tube of polyamide externally tapered about the distal end and jacketed by a urethane material. The urethane material is internally tapered to match the externally tapered inner tube and extends beyond the distal end of the inner tube to form a flexible tip. Although well-suited as an angiographic catheter to withstand high burst pressures of injected contrast medium, the thickness of the catheter walls severely limits the use of this catheter as a guiding catheter through which an angioplasty balloon catheter is commonly inserted. The lumen of a guiding catheter must be as large as possible with a correspondingly thin catheter wall that can be pushed and guided through tortuous coronary vessels without causing trauma thereto.

One guiding catheter includes a wire-braided Teflon material inner tube with a polyurethane jacket epoxied thereto that abruptly terminates near the distal end of the inner tube. A metal radiopaque marker and a soft polyurethane tip are positioned around the distal end of the Teflon material inner tube and abut the abrupt, step-like shoulder at the distal end of the polyurethane jacket. The polyurethane tip is thermally bonded to the polyurethane jacket. A problem with this design is that the contact surface area between the abrupt, step-like shoulder of the polyurethane jacket and the proximal end of the polyurethane tip is limited, thereby significantly increasing the likelihood that the tip will be dislodged or separated from the step-like shoulder of the jacket. The metal radiopaque marker positioned between the jacket and tip further reduces the contact surface area therebetween and increases the likelihood of jacket and tip separation.

SUMMARY OF THE INVENTION

The foregoing problems are solved and a technical advance is achieved in an illustrative guiding catheter having a main tubular portion and a soft tip with respective matching external and internal tapers for advantageously increasing the bonding area and minimizing the likelihood of separation therebetween. Furthermore, the tapers provide a gradual change in durometer between the soft tip and main tubular portion. The main tubular portion includes a layered wall between its outer surface and inner passageway surface extending longitudinally therein. The wall has a composite durometer and advantageously includes an inner material layer for lubricous insertion of other catheters therethrough and an outer material layer for increasing the compression strength and pushability of the catheter through coronary vessels. The outer layer extends the entire length of the external taper, whereas the inner layer longitudinally extends partially along the external taper to strengthen the bond between the tapers. The tubular tip comprises material having a durometer softer than the durometer of the main tubular portion for minimizing trauma to vessel walls. The proximal end of the tubular tip includes the internal taper that is bonded to the external taper of the main tubular portion.

Furthermore, the soft, tubular tip cooperates with the harder durometer main portion by readily bending in tortuous vessels when pushed therethrough. The wall of the main portion further includes a reinforcing braid for enhancing the torquability of the catheter and for minimizing kinking of the catheter when flexed. The braid also extends partially into the tapered section of the main portion to further strengthen the bond between the main portion and soft tip. The combination of the inner and outer layers with the braid therebetween also reduces the thickness of the wall to within a range of 0.006" to 0.0155" depending on the outside diameter of the catheter.

The inner layer of the wall comprises preferably polytetrafluoroethylene having an approximately 50 to 65 hardness durometer on the Shore D scale. This lubricous inner layer material also prevents the braid from extending into the passageway and presenting a rippled surface on which a passing catheter may undesirably engage. The outer layer of the wall preferably comprises polyether block amide including by weight 10 to 30 percent radiopaque bismuth, which is softer in durometer than the composite durometer of the catheter as well as that of the inner wall material. The soft, tubular tip comprises another polyether block amide that is softer in durometer than the outer wall material and advantageously includes by weight 35 to 65 percent tungsten for increasing the radiopacity of the soft tip.

In particular, the illustrative 8 French guiding catheter has a uniform outside diameter of approximately 0.103", a uniform inside diameter of approximately 0.082", and a wall thickness of nominally 0.0105" for inserting the largest possible angioplasty balloon catheter therethrough. The tubular tip has an internal taper extending longitudinally in a range of 2 to 3 mm with the inner layer of the main portion extending partially therealong in a range of 1 to 2 mm.

BRIEF DESCRIPTION OF THE DRAWING

FIG. 1 depicts a partially cross-sectioned view of an illustrative soft tip guiding catheter of the present invention for atraumatic insertion through coronary vessels and introduction of an angioplasty balloon catheter therethrough; and FIG. 2 depicts a partially cross-sectioned view of the wall of the guiding catheter of FIG. 1.

DETAILED DESCRIPTION

FIG. 1 depicts a partially cross-sectioned view of illustrative soft tip guiding catheter 10 having main tubular portion 11 and soft tubular tip 12 with thermal bond 15 interconnecting mated external and internal tapers 13 and 14, respectively. The inner and outer diameters of the main portion are uniform and match those of the soft tip for inserting the largest possible angioplasty balloon catheter therethrough and providing a uniform outer catheter surface for ready insertion through a coronary vessel. Multilayered catheter wall 21 of the main portion includes lubricous inner layer 25 and compression resistant outer layer 27. Reinforcing braid 26 is positioned around inner layer 25 for making the thin catheter wall torquable and minimizing kinking when directing the catheter through tortuous coronary vessels. The composite durometer such as 48 on the Shore D scale of the main portion is hard so as to advance the catheter to the coronary vessels. The soft durometer tip minimizes vessel wall trauma. The internal and external tapers increase the strength of thermal bond 15 to prevent separation from the main portion and also provide a gradual change in the durometer of the catheter between the main portion and tubular tip.

The soft tip includes proximal end 22 with internal taper 14, distal end 23, and passageway 24 extending longitudinally therethrough. Wall 33 of the tubular tip extends between inner passageway surface 31 and outer surface 32. The soft tip preferably comprises a soft durometer polyether block amide material such as nylon with a durometer of approximately 75 on the Shore A scale and having by weight in a range of 35 to 65 percent tungsten. The tungsten significantly increases the radiopacity of the soft tip. Preferably, soft tip 12 is a 2 cm length of 7.8 French nylon material tube including by weight 50 percent nylon and 50 percent tungsten. Internal taper 14 extends longitudinally approximately 2 to 3 mm about distal end 23. Distal end 23 is rounded inside and out for presenting an atraumatic end surface. Thermal bond 15 between external and internal tapers 13 and 14 is formed using any of a number of well-known techniques.

The main portion includes proximal end 16, distal end 17 with external taper 13, and passageway 18 extending longitudinally therethrough communicating with passageway 24 of the soft tip. Wall 21 extends between inner passageway surface 19 and outer surface 20. Outer surface 20 and inner surface 19 of the main portion have respective diameters approximating the respective diameters of outer surface 32 and inner surface 31 of the soft tip. As a result, the guiding catheter has a smooth, uniform outer surface for ready and atraumatic insertion through coronary vessels and a smooth, uniform inner passageway surface for introducing the largest possible angioplasty balloon catheter therethrough. Guiding catheter 10 preferably has a uniform 8 French outside diameter of approximately 0.103", a uniform inside diameter of approximately 0.082", and a wall nominally 0.0105" in thickness. Well-known connector cap 28 and winged flange 29 are fixedly attached about proximal end 16 of the main portion by a commercially available, medical grade adhesive, 30 such as Loctite No. 401, for providing a handle to manipulate the catheter.

FIG. 2 depicts a partially cross-sectioned view of main portion wall 21 and soft tip wall 33. Soft tip wall comprises 50 percent polyether block amide for atraumatic insertion and 50 percent tungsten, shown as particles 34, for radiopacity.

Main portion wall 31 includes inner layer 25, reinforcing braid 26, and outer layer 27. Inner layer 25 comprises a lubricous material such as polytetrafluoroethylene having an approximately 50 to 65 durometer on the Shore D scale for providing a slick inner passageway surface. To increase the strength of thermal bond 15, the inner layer longitudinally extends partially along external taper 13, which is approximately 2 to 3 mm in length, for approximately 1 to 2 mm. In the preferred embodiment, inner layer 25 comprises a 130 cm length of 6.7 French polytetrafluoroethylene tube.

The main portion wall further includes reinforcing braid 26 of, for example, stainless steel wire, for enhancing the torquability and kink resistance of the catheter. The braid also longitudinally extends partially along the external taper for further strengthening the bond thereat. In the preferred embodiment, braid 26 is 175 cm long with an outside diameter of 0.078" and having a pic of 50 formed of 0.0026" and 0.0030" diameter Series 304 stainless steel wire. Inner layer 25 prevents the braid from rippling inner passageway surface 19 and undesirably engaging another catheter being passed therethrough.

The main portion wall further comprises outer layer 27 longitudinally extending the entire length of the external taper. The outer layer preferably also comprises a polyether block amide such as nylon for increasing the compression strength and pushability of the catheter and includes by weight in a range of 10 to 30 percent bismuth, shown by particles 35, for radiopacity. The polyether block amide material of the outer layer is softer in durometer than the composite durometer of the catheter as well as that of the inner layer. In particular, outer layer 27 is a 130 cm length of 9 French nylon material tube comprising by weight approximately 90 percent nylon with a durometer of approximately 60.7 on the Shore D scale and 10 percent bismuth. The combination of the inner and outer layers with the braid positioned therebetween comprises a wall thickness in a range of 0.006" to 0.0155" depending on the outside diameter of the catheter and has a composite durometer of approximately 48 on the Shore D scale. Multilayered wall 21 is thermally bonded using any of a number of well-known techniques.

It is to be understood that the above-described soft tip guiding catheter is merely an illustrative embodiment of the principles of this invention and that other embodiments may be devised by those skilled in the art without departing from the spirit and scope of this invention. It is contemplated that various other materials of comparable durometers may be utilized for the inner or outer layers, reinforcing braid, or soft tip. In summary, the combination of material layers in the main portion of the guiding catheter provides a thin wall with pushability, torquability, and kink resistance. The soft tip thermally bonded to the main portion by respective tapers presents a soft, atraumatic surface to delicate coronary vessels.

What is claimed is:

1. A soft tip guiding catheter comprising:
   a main, tubular portion having a distal end and a first passageway extending longitudinally therethrough, said portion further including a first outer surface, a first inner passageway surface, and a wall having a composite durometer therebetween, said distal end having an external taper extending between said first inner passageway surface and said first outer surface, said wall including an outer material layer forming the entire length of said external taper and an inner material layer longitudinally extending partially into a region of the external taper and bonded to said outer material layer; and
   a tubular tip comprising a material having a durometer softer than said composite durometer, said tip having a proximal end and a second passageway extending longitudinally therethrough communicating with said first passageway, said proximal end having an internal taper bonded to said external taper of said distal end of said main tubular portion.

2. The guiding catheter of claim 1 wherein said tubular tip includes a second outer surface having a diameter approximating that of said first outer surface and further includes a second inner passageway surface having a diameter approximating that of said first inner passageway surface.

3. The guiding catheter of claim 1 further including a thermal bond between said external and internal tapers.

4. The guiding catheter of claim 1 wherein said wall has a thickness in the range of 0.006" to 0.0155".

5. The guiding catheter of claim 1 wherein said wall further includes a braid positioned around and along said inner layer.

6. The guiding catheter of claim 5 wherein said braid comprises stainless steel wire.

7. The guiding catheter of claim 1 wherein said taper extends longitudinally in a range of 2 to 3 mm.

8. The guiding catheter of claim 7 wherein said inner material layer longitudinally extends approximately in a range of 1 to 2 mm along said external taper.

9. The guiding catheter of claim 1 wherein said inner layer comprises polytetrafluoroethylene.

10. The guiding catheter of claim 9 wherein said outer layer comprises a first polyether block amide material having a first durometer.

11. The guiding catheter of claim 10 wherein said material of said tubular tip comprises a second polyether block amide material having a second durometer softer than said first durometer.

12. The guiding catheter of claim 11 wherein said material of said tubular tip further comprises tungsten.

13. The guiding catheter of claim 10 wherein said outer layer further includes bismuth.

14. A soft tip guiding catheter comprising:
a main, tubular portion having a distal end and a first passageway extending longitudinally therein, said portion further including a first outer surface, a first inner passageway surface, and a wall therebetween, said distal end having an external taper extending between said first inner passageway surface and said first outer surface, said wall having an inner layer of a first material having a first durometer and longitudinally extending partially into a region of the external taper, an outer layer of a second material having a second durometer softer than said first durometer and forming the entire length of said external taper, and a reinforcing braid positioned between said inner and outer layers; and
a tubular tip comprising a third material having a third durometer softer than said second durometer, said tip having a proximal end and a second passageway extending therein and communicating with said first passageway, said proximal end having an internal taper bonded to said external taper of said distal end of said main tubular portion.

15. The guiding catheter of claim 14 wherein said tubular tip includes a second outer surface having a diameter approximating that of said first outer surface and includes a second inner passageway surface having a diameter approximating that of said first inner passageway surface.

16. The guiding catheter of claim 14 further including a thermal bond between said eternal and internal tapers.

17. The guiding catheter of claim 14 wherein said outer layer includes by weight in a range of 10 to 30 percent bismuth and a remaining percentage of polyether block amide.

18. The guiding catheter of claim 17 wherein said third material comprises by weight in a range of 35 to 65 percent tungsten and a remaining percentage of polyether block amide.

19. The guiding catheter of claim 17 wherein said first material comprises polytetrafluoroethylene.

20. A soft tip guiding catheter comprising:
a main, tubular portion having a distal end and a first passageway extending longitudinally therein, said portion further including a wall having a thickness in the range of 0.006" to 0.0155" between a first outer surface and a first inner passageway surface thereof, said distal end having an external taper extending between said first inner passageway surface and said first outer surface, said wall having an inner layer of polytetrafluoroethylene having a first durometer and longitudinally extending partially into a region of the external taper and an outer layer by weight of approximately 90 percent polyether block amide and 10 percent bismuth having a second durometer softer than said first durometer and forming the entire length of said external taper, said wall further including a stainless steel wire braid longitudinally extending partially into a region of the external taper and positioned between said inner and outer layers and around said inner layer; and
a tubular tip comprising by weight approximately 50 percent polyether block amide and 50 percent tungsten and having a third durometer softer than said second durometer, said tip having a proximal end and a second passageway extending therein and communicating with said first passageway, said proximal end having an internal taper thermally bonded to said external taper of said distal end of said main tubular portion, said tubular tip including a second outer surface having a diameter approximating that of said first outer surface and including a second inner passageway surface having a diameter approximating that of said first inner passageway surface.

* * * * *